United States Patent
Tsumura et al.

(10) Patent No.: US 11,124,420 B2
(45) Date of Patent: Sep. 21, 2021

(54) POWDERED GYROLITE-TYPE CALCIUM SILICATE HAVING HIGH OIL ABSORBENCY AND LARGE PARTICLE DIAMETER, AND PRODUCTION METHOD THEREFOR

(71) Applicant: TOMITA PHARMACEUTICAL CO., LTD., Naruto (JP)

(72) Inventors: Yuuta Tsumura, Naruto (JP); Kazuki Kamai, Naruto (JP); Yukinori Konishi, Naruto (JP); Kazuhiko Tamagawa, Naruto (JP)

(73) Assignee: TOMITA PHARMACEUTICAL CO., LTD., Naruto (JP)

( * ) Notice: Subject to any disclaimer, the term of this patent is extended or adjusted under 35 U.S.C. 154(b) by 0 days.

(21) Appl. No.: 15/034,912

(22) PCT Filed: Nov. 7, 2014

(86) PCT No.: PCT/JP2014/079551
§ 371 (c)(1),
(2) Date: May 6, 2016

(87) PCT Pub. No.: WO2015/068793
PCT Pub. Date: May 14, 2015

(65) Prior Publication Data
US 2016/0289081 A1    Oct. 6, 2016

(30) Foreign Application Priority Data
Nov. 9, 2013 (JP) .............................. JP2013-232622

(51) Int. Cl.
*C01B 33/24* (2006.01)
*A61K 9/51* (2006.01)
*A23L 29/00* (2016.01)
*A61K 9/16* (2006.01)
*A61K 47/02* (2006.01)

(52) U.S. Cl.
CPC ............ *C01B 33/24* (2013.01); *A23L 29/015* (2016.08); *A61K 9/1611* (2013.01); *A61K 9/5115* (2013.01); *A61K 47/02* (2013.01); *A23V 2002/00* (2013.01); *C01P 2004/61* (2013.01); *C01P 2006/19* (2013.01)

(58) Field of Classification Search
CPC .... A61K 9/1611; A61K 9/5115; A61K 47/02; A23L 29/015; C01B 33/24; C01P 2006/19; C01P 2004/61; A23V 2002/00
See application file for complete search history.

(56) References Cited

U.S. PATENT DOCUMENTS

| | | | | |
|---|---|---|---|---|
| 4,226,636 A | * | 10/1980 | Mizutani | C01B 33/24 |
| | | | | 106/470 |
| 8,679,547 B2 | * | 3/2014 | Konishi | A61K 33/06 |
| | | | | 423/331 |

FOREIGN PATENT DOCUMENTS

JP    2013-227205    * 11/2013

* cited by examiner

*Primary Examiner* — Lezah Roberts
(74) *Attorney, Agent, or Firm* — Locke Lord LLP

(57) ABSTRACT

Provided is powdered gyrolite-type calcium silicate that has a relatively large particle size, yet is endowed with both a high oil absorption and a high particle strength. The powdered gyrolite-type calcium silicate has (1) an oil absorption of at least 2.8 mL/g, (2) an average particle diameter of at least 40 μm, and (3) in treatment where the gyrolite-type calcium silicate is charged into a laser diffraction-type particle size analyzer within the range of a diffraction volume of from 0.1 to 0.6 and circulated at a flow rate of 32.5 mL/s for 5 minutes, a percent change in average particle diameter following treatment with respect to average particle diameter before treatment of 15% or less.

12 Claims, 2 Drawing Sheets

[Fig. 1]
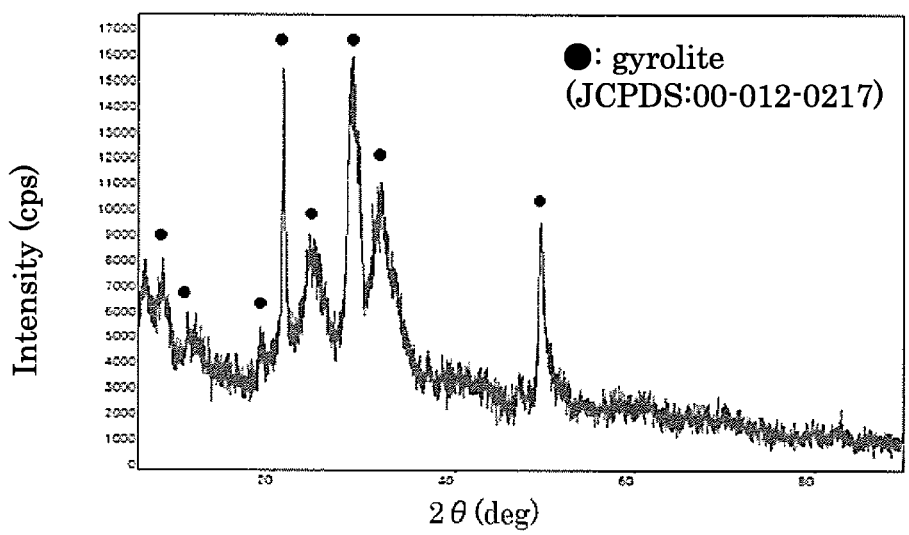
[Fig. 2]
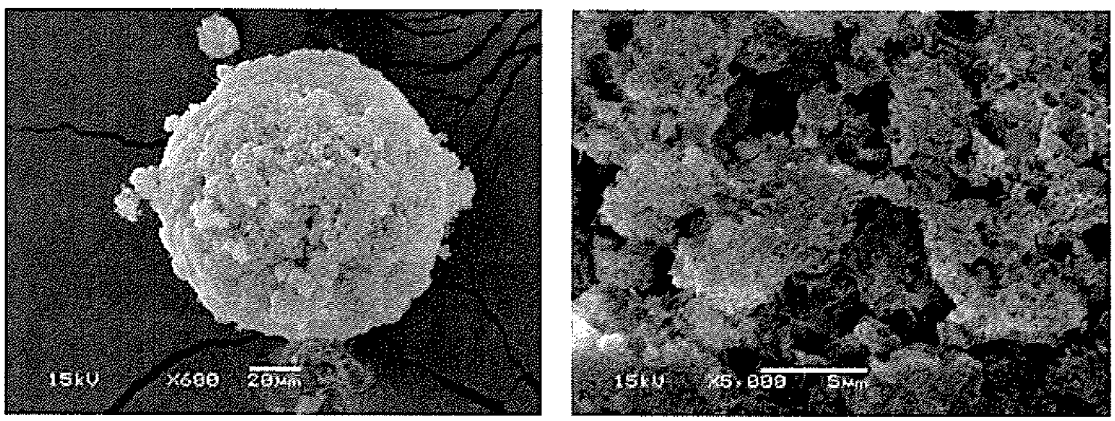
[Fig. 3]
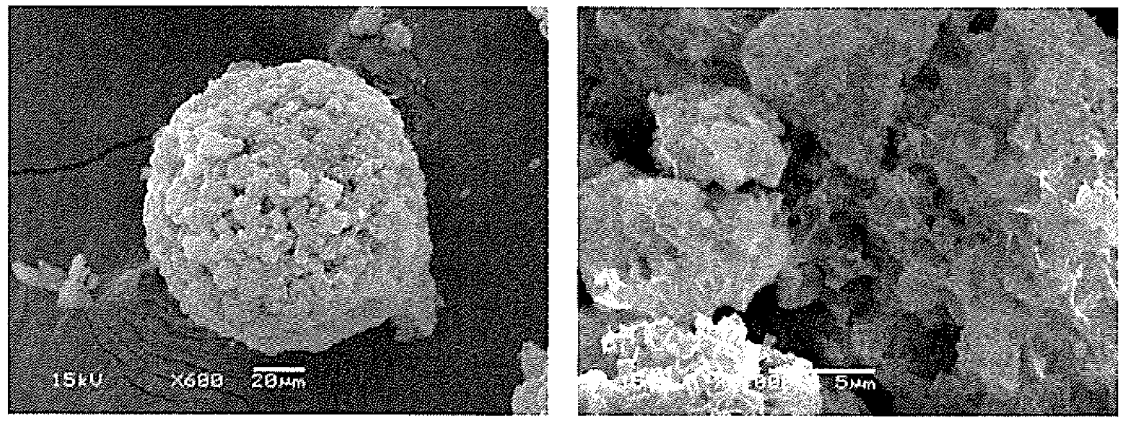

[Fig. 4]
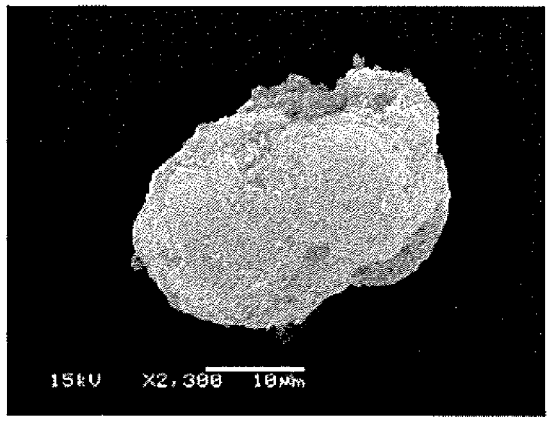 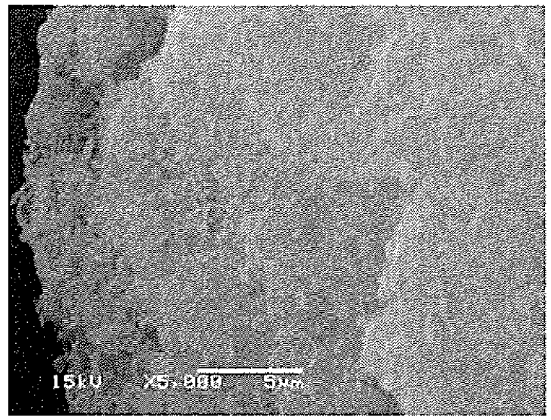
[Fig. 5]
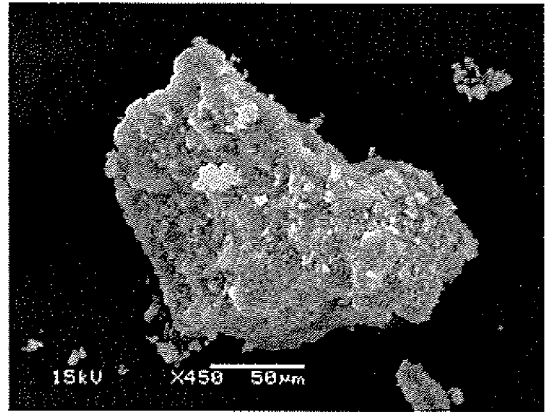 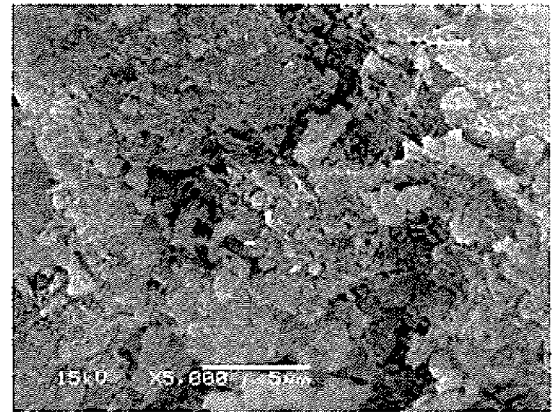
[Fig. 6]
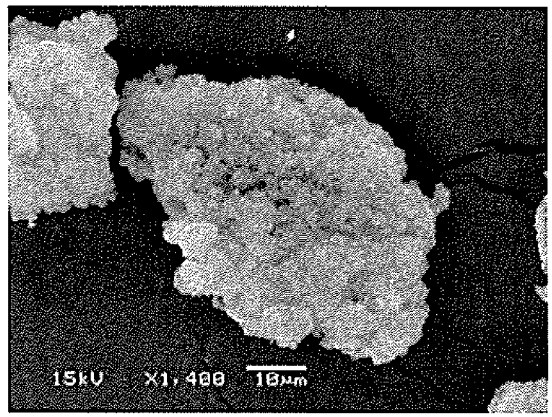 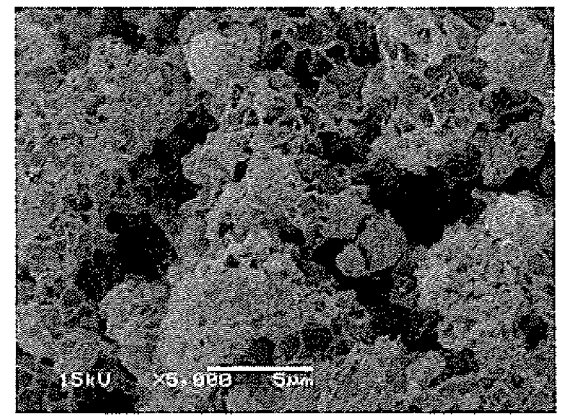

POWDERED GYROLITE-TYPE CALCIUM SILICATE HAVING HIGH OIL ABSORBENCY AND LARGE PARTICLE DIAMETER, AND PRODUCTION METHOD THEREFOR

BACKGROUND OF THE INVENTION

1. Field of the Invention

This invention relates to powdered gyrolite-type calcium silicate, and to a method of manufacturing the same.

2. Description of the Related Art

Calcium silicate is a compound that has long been known, and exists both as natural products and as synthetic products. The crystal forms of calcium silicate include gyrolite, wollastonite and tobermorite. Calcium silicate is utilized in various applications, including not only construction materials (lagging, refractory materials, thermal insulation, etc.), but also as, for example, drug additives, food additives, fillers, thickening agents, delusterants and carriers. Of these various types of calcium silicate, those calcium silicates which have a high oil absorption in particular are used as drug additives, such as excipients, carriers, binders and disintegrants, in addition to which they are used as carriers for liquid substances in the cosmetics field or industrial field. They are used in particular as a carrier for deoxidizing agents.

Among the common methods known for producing such calcium silicate is the method of manufacturing calcium silicate or a calcium silicate-gypsum composite disclosed in Japanese Patent Application Publication No. S56-5317, which method is characterized by including the steps of mixing and reacting gypsum and an alkali silicate in an aqueous medium, washing the solids obtained in the reaction step, rendering the solids obtained in the washing step into a slurry, hydrothermally treating the slurry obtained in the slurry forming step, and separating off the calcium silicate or the calcium silicate-gypsum composite obtained in the hydrothermal treatment step.

In addition, Japanese Patent Application Publication Nos. S54-93698, 2013-87052, H06-239611 and H09-30812 disclose methods of producing calcium silicate by the hydrothermal treatment of aqueous slurries composed of a silicate feedstock and a calcium feedstock. Also, Japanese Patent Application Publication No. 2003-144113 and Japanese Patent No. 4305664 describe methods of obtaining large-particle-size calcium silicate granulated materials having an average particle diameter of at least 100 μm by adding binder and the like to a calcium silicate powder, and carrying out treatment such as mixing and granulation.

Of the calcium silicate produced by such methods, calcium silicate having a gyrolite-type crystal structure (unless noted otherwise, referred to below as "gyrolite-type calcium silicate") in particular has a large bulk specific volume and a large oil absorption compared with other crystal forms of calcium silicate. Hence, gyrolite-type calcium silicate is used in such applications as an additive for preventing the adherence and improving the flow of dehumidifying agents, a carrier for impregnation with liquid substances, a forming aid, an adsorbent, food additives, drug additives, and the formation of drug preparations.

SUMMARY OF THE INVENTION

However, although conventional gyrolite-type calcium silicate powder has a high oil absorption, the particle size is small and much of it is in a finely divided form, resulting in a poor handleability. That is, when the flowability during powder filling using a filling machine is poor, problems such as high powder scattering arise. To improve handleability, it is useful for the powder to be composed of large-diameter particles and moreover essential for the particles making up the powder to be nearly spherical in shape.

A large particle size can conceivably be obtained by carrying out a mixing/granulating operation such as tumbling granulation, extrusion granulation or dry compression granulation using a powder. However, when an attempt is made to carry out granulation while maintaining a given particle strength, the particles incur physical pressure during granulation, as a result of which the interior of the granulated material densifies, lowering the oil absorption. On the other hand, if a granulated material is produced in such a way as to prioritize the oil absorption and is not dense, the desired strength is not achieved. Such granules readily disintegrate, making it impossible to maintain a large particle size and leading to powdering of the material, as a result of which the handleability cannot be improved. This problem is the same even in cases where a calcium silicate granulated material is used as a carrier (liquid-absorbing carrier). With conventional gyrolite-type calcium silicate granulated materials, in an impregnating step in which a liquid or the like is impregnated or in a subsequent granulating step, problems such as bleeding of the impregnated liquid arise on account of the low oil absorption.

Therefore, there has existed a need for the development of a gyrolite-type calcium silicate powder which, without requiring a special granulating step, has a large particle size yet also has a high oil absorption and a high particle strength, and is thus capable of exhibiting a good handleability. However, gyrolite-type calcium silicate powders having these particular qualities have not hitherto been developed.

It is therefore an object of the present invention to provide powdered gyrolite-type calcium silicate which has a relatively large particle size, yet is endowed with both high oil absorption and high particle strength.

The inventors have conducted extensive research in order to resolve the above problems. As a result, they have discovered that calcium silicate powder produced by a specific method has excellent properties, and is thus able to achieve the above objects.

Accordingly, the present invention relates to the following powdered gyrolite-type calcium silicate, and the following method of manufacturing powdered gyrolite-type calcium silicate:

1. Powdered gyrolite-type calcium silicate having:

(1) an oil absorption of at least 2.8 mL/g;

(2) an average particle diameter of at least 40 μm; and (3) in treatment where the gyrolite-type calcium silicate is charged into a laser diffraction-type particle size analyzer within the range of a diffraction volume of from 0.1 to 0.6 and circulated at a flow rate of 32.5 mL/s for 5 minutes, a percent change in average particle diameter following treatment with respect to average particle diameter before treatment of 15% or less.

2. The powdered gyrolite-type calcium silicate according to item 1, having an angle of repose of 45° or less.

3. The powdered gyrolite-type calcium silicate according to item 1, which is composed of particles obtained by spray drying.

4. A method of manufacturing powdered gyrolite-type calcium silicate, the method including the steps of:

(1) preparing a calcium-containing liquid feedstock by adding and mixing together gypsum and a calcium compound other than gypsum in an aqueous solvent;

(2) mixing the calcium-containing liquid feedstock with a silicic acid-containing feedstock to obtain a reaction product;

(3) subjecting an aqueous slurry containing the reaction product to a hydrothermal synthesis reaction to obtain gyrolite-type calcium silicate; and (4) spray-drying a dispersion liquid containing the gyrolite-type calcium silicate to obtain a gyrolite-type calcium silicate powder.

5. The manufacturing method according to item 4, wherein the content of the calcium compound other than gypsum is from 0.11 to 1.99 moles per mole of gypsum.

6. The manufacturing method according to item 4, wherein the calcium compound other than gypsum is at least one of 1) calcium hydroxide, and 2) a calcium compound that reacts with an alkali ingredient to form calcium hydroxide.

7. The manufacturing method according to item 6, wherein the calcium compound that reacts with an alkali ingredient to form calcium hydroxide is at least one of calcium chloride, calcium nitrate and calcium oxide.

8. The manufacturing method according to item 4, including no granulation step other than spray drying.

9. The manufacturing method according to item 4, wherein an aluminum compound has been added to the calcium-containing liquid feedstock and/or the silicic acid-containing feedstock.

10. The manufacturing method according to item 4, wherein the powdered gyrolite-type calcium silicate obtained thereby is the powdered gyrolite-type calcium silicate according to item 1.

11. A product including a chemical substance supported on the powdered gyrolite-type calcium silicate according to any one of items 1 to 3.

12. A drug composition comprising the powdered gyrolite-type calcium silicate according to any one of items 1 to 3.

Advantages of the Present Invention

The present invention makes it possible to provide powdered gyrolite-type calcium silicate which, although having a relative large particle size, can exhibit a good oil absorption and a practical particle hardness. That is, the powdered gyrolite-type calcium silicate of the present invention has a relatively large particle size and moreover is endowed with both a high oil absorption and a high particle strength.

In conventional gyrolite-type calcium silicate, to enhance the handleability while sacrificing the oil absorption properties, it is necessary to increase the particle size by way of operations such as mixing and granulation. By contrast, the powdered gyrolite-type calcium silicate of the present invention has a relatively large particle size and a high particle strength without passing through operations such as mixing and granulation, enabling the large particle size to be maintained. As a result, the occurrence of dusting due to disintegration of the particles can be effectively reduced, enabling excellent handleability as well as flowability to be exhibited. In addition, because the powdered gyrolite-type calcium silicate of the present invention has a high oil absorption, applications are not limited, making use in a broad range of applications possible.

Also, in the production method of the present invention, because gypsum and a calcium compound other than gypsum are used together as the starting materials and particles are prepared by spray-drying a dispersion liquid containing gyrolite-type calcium silicate synthesized by such combined use, this method can efficiently produce powdered gyrolite-type calcium silicate which has a relatively large particle size and is also capable of exhibiting at the same time a high particle strength, a high oil absorption and a high flowability.

The powdered gyrolite-type calcium silicate of the present invention having a high oil absorption, an effective degree of hardness and a large particle size can thus be used in known or commercial calcium silicate applications and similar applications. Especially, given such properties, preferred use can be made particularly in drug additives, food additives, cosmetics raw materials and chemical products. The powdered gyrolite-type calcium silicate of the present invention is especially ideal as a carrier (e.g., a liquid-absorbing carrier), or as an excipient, disintegrant, binder or the like in drugs. For example, preferred use can be made as a carrier (liquid-absorbing carrier) in pharmaceutical preparations containing the calcium silicate of the present invention and drug active ingredients, and in deoxidizing agents and the like.

BRIEF DESCRIPTION OF THE DRAWINGS

FIG. 1 is a graph showing the results obtained by carrying out x-ray diffraction analysis on a sample from Example 3;

FIG. 2 shows scanning electron micrographs of samples from Example 3;

FIG. 3 shows scanning electron micrographs of samples from Example 5;

FIG. 4 shows scanning electron micrographs of samples from Comparative Example 1;

FIG. 5 shows scanning electron micrographs of samples from Comparative Example 2 and FIG. 6 shows scanning electron micrographs of samples from Comparative Example 3.

DESCRIPTION OF THE PREFERRED EMBODIMENTS

1. Powdered Gyrolite-Type Calcium Silicate

The gyrolite-type calcium silicate of the present invention (also referred to below as the "inventive calcium silicate") is powdered gyrolite-type calcium silicate which is characterized by having:

(1) an oil absorption of at least 2.8 mL/g;

(2) an average particle diameter of at least 40 µm; and (3) in treatment where the gyrolite-type calcium silicate is charged into a laser diffraction-type particle size analyzer so as to fall within a range of a diffraction volume (DV value) from 0.1 to 0.6 and circulated at a flow rate of 32.5 mL/s for 5 minutes, a percent change in an average particle diameter following the treatment with respect to an average particle diameter before the treatment of 15% or less. Accordingly, the inventive calcium silicate is characterized by being a crystalline calcium silicate in which the crystal form (crystal structure) is a gyrolite-type crystal structure and by having both a good oil absorption and a practical degree of hardness in spite of having a relatively large particle size.

As mentioned above, the inventive calcium silicate has a crystal form (crystal structure) that is a gyrolite-type crystal structure. This can be confirmed by, as shown in FIG. 1 for example, the peak that appears at a specific refraction angle ($2\theta$) from the results of x-ray diffraction analysis.

The composition of the inventive calcium silicate is not particularly limited so long as it has a gyrolite-type crystal structure, although it can typically be one having the general formula $2CaO \cdot 3SiO_2 \cdot mSiO_2 \cdot nH_2O$ (where m and n are positive numbers, and $0.1 \leq m \leq 10$, n is positive number.). Accordingly, ingredients other than the inventive calcium silicate (gyrolite-type calcium silicate), such as amorphous silicon dioxide and the like, may also be present as long as they do not substantially adversely affect the advantages of the present invention.

The inventive calcium silicate has an oil absorption of at least 2.8 mL/g, and preferably at least 3.0 mL/g. At an oil absorption below 2.8 mL/g, when the calcium silicate is used as, for example, a carrier for various types of chemical substances (drugs, etc.) having given physicochemical properties, because the amount of such substances that can be supported is limited, the properties and performance per unit volume expected of these chemical substances are unlikely to be fully achieved. There is no restriction on the upper limit in the oil absorption, although the upper limit is generally set to about 6.0 mL/g.

The average particle diameter of the inventive calcium silicate may be suitably set according to, for example, the intended applications and method of use for the inventive calcium silicate, but may be at least 40 μm, and may be preferably at least 60 μm, and more preferably at least 70 μm. Because the inventive calcium silicate has a relatively large particle diameter, a powder of excellent handleability can be provided. In the conventional art, owing in part to the fact that, to obtain a gyrolite-type calcium silicate granulated material having a given particle strength and also having a large particle diameter, such a granulated material is produced by a granulation method other than spray drying, such a conventional calcium silicate granulated material is dense, which makes it difficult to achieve a practically useful oil absorption. By contrast, a major advantage of the inventive calcium silicate is that, although it has a relatively large particle diameter, it possesses both a good oil absorption and a practical degree of hardness. There is no restriction on the upper limit in the average particle diameter of the inventive calcium silicate, although the upper limit in the average particle diameter is typically about 1,500 μm, and may be set to preferably 500 μm or less, and more preferably 300 μm or less.

The calcium silicate of the present invention has, in treatment where the calcium silicate is charged into a laser diffraction-type particle size analyzer so that a DV value may be in a range of 0.1-0.6 and circulated at a flow rate of 32.5 mL/s for 5 minutes, a percent change in an average particle diameter following the treatment with respect to an average particle diameter before the treatment (abbreviated below as simply "percent change") of 15% or less, and preferably 10% or less. The lower this value, the more resistant the particles are to disintegration, indicating that the particle strength is higher and, such higher strength is long-lasting even in an aqueous medium. Hence, this is an effective method of evaluation, particularly when it is presumed that the inventive calcium silicate will be used as a carrier (liquid absorbing carrier). That is, the particles making up the inventive calcium silicate (powder) have the advantages of an excellent particle strength and resistance to disintegration, and moreover lend themselves well to use as a carrier (liquid-absorbing carrier). Because the inventive calcium silicate is able to maintain substantially the same particle diameter as the particle diameter immediately after spray drying, dusting caused by disintegration of the particles can be effectively reduced, as a result of which it is possible for the high handleability that is an advantage of a large particle diameter to be sustained.

The inventive calcium silicate is preferably composed of particles obtained by spray-drying, and is more preferably gyrolite-type calcium silicate obtained by the inventive production method described below in Section 2.

The inventive calcium silicate can be used in various applications in the same way as conventional gyrolite-type calcium silicate. For example, it can be suitably used as a carrier for supporting chemical substances (deoxidizing ingredients, catalyst active material, drug active ingredients, etc.), or as an excipient (or filler) contained in drug compositions. These can be used by the same methods as conventional gyrolite-type calcium silicate. Accordingly, products in which a chemical substance is supported on the inventive calcium silicate, and drug compositions containing the inventive calcium silicate are also encompassed by the present invention.

2. Method of Manufacturing Inventive Calcium Silicate

The inventive calcium silicate can be suitably manufactured by, in particular, the method of manufacture described below. That is, the inventive calcium silicate can be suitably manufactured by a method of manufacturing powdered gyrolite-type calcium silicate which is characterized by including the steps of:

(1) preparing a calcium-containing liquid feedstock by adding and mixing together gypsum and a calcium compound other than gypsum in an aqueous solvent (Ca liquid feedstock preparation step);

(2) mixing the calcium-containing liquid feedstock with a silicic acid-containing feedstock to obtain a reaction product (reaction step);

(3) subjecting an aqueous slurry containing the reaction product to a hydrothermal synthesis reaction to obtain gyrolite-type calcium silicate (hydrothermal treatment step); and (4) spray-drying a dispersion liquid containing the gyrolite-type calcium silicate to obtain a gyrolite-type calcium silicate powder (spray-drying step).

Calcium (Ca) Liquid Feedstock Preparation Step

In the Ca liquid feedstock preparation step, a calcium-containing liquid feedstock is prepared by adding and mixing gypsum and a calcium compound other than gypsum to an aqueous solvent.

The gypsum used may be similar to that used in the production of known calcium silicates. For example, use can be made of gypsum anhydrite, gypsum hemihydrate, gypsum dihydrate and the like. In this invention, the use of gypsum dihydrate is especially preferred.

The calcium compound other than gypsum (also referred to below as the "second calcium compound") is not particularly limited, provided it is a compound containing calcium. For example, hydroxides, salts (inorganic acid salts or organic acid salts) and the like can be used. More specifically, preferred use can be made of, for example, calcium hydroxide, and also calcium compounds which react with an alkali ingredient to form calcium hydroxide. In particular, at least one of calcium oxide, calcium chloride, calcium nitrate and the like may be used as the calcium compound which reacts with an alkali ingredient to form calcium hydroxide. In the manufacturing method of the present invention, by thus using a second calcium compound as a calcium source as well as gypsum, the inventive calcium silicate described above in Section 1 can be reliably obtained. That is, particles having a large particle diameter and moreover endowed with both a high oil absorption and a large particle strength can be produced, as a result of which it is possible to obtain powdered gyrolite-type calcium silicate having decreased dusting properties and an excellent handleability.

The compounding ratio of the gypsum and the second calcium compound is not particularly limited, although the content of the second calcium compound per mole of gypsum is preferably set to from 0.11 to 1.99 moles, and more preferably from 0.2 to 1.5 moles. By setting the compounding ratio in this way, particles endowed with a high oil absorption and flowability and also having a high particle strength can be prepared.

The calcium-containing liquid feedstock is obtained by adding and mixing the gypsum and the second calcium compound in an aqueous solvent. At least one solvent from among water and water-soluble organic solvents may be used as the aqueous solvent. Illustrative examples of water-soluble organic solvents that may be used include alcohols such as methanol, ethanol and propanol, and also acetone and the like. In the practice of the present invention, the use of water is especially preferred. The amount of aqueous solvent used is not particularly limited and generally may be suitably adjusted so that the solids concentration of the liquid feedstock is from about 1 to about 30 wt %, and preferably from about 1 to about 20 wt %.

Also, in the production method of the present invention, the gypsum and the second calcium compound may be dissolved within the aqueous solvent, or may be in a dispersed state. In particular, it is desirable for the second calcium compound to be dissolved in the aqueous solvent.

Reaction Step

In the reaction step, the calcium-containing liquid feedstock and a silicic acid-containing feedstock are mixed together to obtain a reaction product.

The silicic acid-containing feedstock used may be similar to that used in the production of known calcium silicates. For example, sodium silicate, potassium silicate, silica sol or the like can be used.

The mixing ratio of the silicic acid-containing feedstock and the calcium-containing liquid feedstock may be set in such a way that the desired calcium silicate forms. For example, stoichiometrically, the Si/Ca molar ratio can be set in the range of preferably from 1.5 to 2.9, and more preferably from 1.5 to 2.3.

Other raw materials (additives) may be optionally included in the reaction system so as to not adversely affect the advantages of the present invention. For example, a pH adjustor such as hydrochloric acid, sulfuric acid or sodium hydroxide can be used.

In particular, in the practice of this invention, from the standpoint of more reliably obtaining powdered gyrolite-type calcium silicate having the properties indicated in Section 1 above, it is preferable for an aluminum ingredient to be included in the calcium-containing liquid feedstock and/or the silicic acid-containing feedstock. An aluminum compound can be used as the source of the aluminum ingredient. Examples of aluminum compounds include at least one from among aluminum salts, aluminum hydroxides and aluminum oxides. More specifically, preferred use can be made of at least one aluminum compound from among sodium aluminate, aluminum chloride and aluminum hydroxide. In cases where an aluminum ingredient is included, the content thereof, expressed as the molar ratio $Al_2O_3/SiO_2$ in the raw materials, is preferably set to at least 0.002, and more preferably set to at least 0.003. The upper limit in this $Al_2O_3/SiO_2$ molar ratio may be suitably set according to, for example, the intended use of the calcium silicate, although in general the upper limit may be set to about 0.04.

The calcium-containing liquid feedstock and the silicic acid containing feedstock (which optionally contains other ingredients) are mixed together in these given compounding proportions. The two are thereby reacted together, enabling a reaction product to be obtained in the form of an aqueous slurry. It is preferable to suitably set the reaction temperature, although not particularly limited, within the range of, e.g., 5 to 100° C., and especially 5 to 40° C. As for the reaction atmosphere, the reaction may be carried out in open air (at atmospheric pressure). The reaction time can be suitably adjusted according to the reaction temperature and other factors. The reaction product can be obtained in this way from the above feedstocks.

The aqueous slurry obtained may be furnished directly as is to the hydrothermal synthesis step or may be furnished to the hydrothermal synthesis after adjustment of the solids concentration. Alternatively, the aqueous slurry may be solid-liquid separated to obtain the solids (reaction product), and then optionally the reaction product may be subjected to water rinsing and the like, following which an aqueous solvent may be freshly added to the reaction product so as to again prepare an aqueous slurry which is then furnished to the hydrothermal treatment step. The aqueous solvent used in this latter case may be the same as the aqueous solvent used in the Ca liquid feedstock preparation step.

Hydrothermal Treatment Step

In the hydrothermal treatment step, gyrolite-type calcium silicate is obtained by subjecting the aqueous slurry comprising the reaction product to a hydrothermal synthesis reaction.

By subjecting the reaction product-containing aqueous slurry to a hydrothermal synthesis reaction, gyrolite-type calcium silicate of the general formula $2CaO.3SiO_2.mSiO_2.nH_2O$ (where m and n are positive numbers, and $0.1 \leq m \leq 10$, n is positive number.) is obtained.

The solids content of the aqueous slurry furnished to the hydrothermal treatment step can be suitably set, although it is generally set to from 1 to 30 wt %, and preferably from 3 to 20 wt %.

In the manufacturing method of the present invention, in order to form gyrolite-type calcium silicate, the temperature of the hydrothermal synthesis reaction is preferably in the range of 150 to 250° C. If this temperature is too low, the formation of gyrolite-type calcium silicate takes time. On the other hand, if the temperature is too high, insufficient formation of gyrolite-type calcium silicate occurs. The reaction time varies according to the reaction temperature and other factors, but generally may be set in the range of 1 to 50 hours.

Because the hydrothermal synthesis reaction involves the treatment of the aqueous slurry at an elevated temperature of at least 150° C., it is carried out within a closed reaction system and under applied pressure. Hence, the hydrothermal treatment step can generally be carried out using a known pressure-resistant reactor (e.g., an autoclave).

Spray-Drying Step

In the spray-drying step, a gyrolite-type calcium silicate powder is obtained by spray-drying a gyrolite-type calcium silicate-containing dispersion liquid (aqueous dispersion liquid).

The aqueous slurry obtained in the hydrothermal treatment step may be used directly as the gyrolite type-calcium silicate-containing dispersion liquid, or the spray-drying step may be carried out after adjustment of the solids concentration of the aqueous slurry. Alternatively, the aqueous slurry may be solid-liquid separated and then the solids (gyrolite-type calcium silicate) obtained may be optionally subjected to water rinsing and the like, following which an aqueous solvent may be freshly added to the gyrolite-type calcium silicate so as to again prepare an aqueous slurry which is then furnished the slurry to the spray-drying step. The aqueous solvent used may be the same as the aqueous solvent used in the Ca liquid feedstock preparation step.

If necessary, the dispersion liquid may be furnished to the spray-drying step after adding therein a third ingredient in a range that does not substantially adversely affect the advantages of the present invention. As the third ingredient, use may be made of, for instance, inorganic compounds such as calcium silicate other than gyrolite-type calcium silicate, silica gel and iron; alcohols such as ethanol and glycerol; binders such as synthetic high molecular weight compounds, soluble cellulose compounds and natural polymer compounds; chemical agents such as compounds having reducing properties including ascorbic acid or the like; and adsorbents such as activated carbon.

There are no limitations on the solids concentration of the dispersion liquid, although this is preferably set to from 3 to 20%, and more preferably from 3 to 10%. By setting the solids concentration in this range, gyrolite-type calcium silicate particles having a large particle diameter can be more reliably produced.

The spray-drying conditions are not particularly limited, although it is generally desirable to carry out spray-drying using a disk or nozzle at an inlet temperature of preferably from 150 to 500° C., and more preferably from 150 to 450° C., and at an outlet temperature of from 50 to 200° C., and more preferably from 50 to 180° C. During spray-drying, a known or commercially available spray drying apparatus may be used. By spray-drying a dispersion of the gyrolite-type calcium silicate synthesized using both gypsum and a second calcium compound, powdered gyrolite-type calcium silicate having a high oil absorption and a high particle strength, and also having a relatively large particle diameter can be effectively obtained.

If necessary, additional operations such as classification may be carried out on the gyrolite-type calcium silicate that has been recovered. However, to more reliably maintain the properties mentioned above, it is desirable that granulation steps other than spray drying not be carried out.

EXAMPLES

The present invention is described more fully below by way of working examples and comparative examples, although the scope of the present invention is not limited by the examples. Unless noted otherwise, all references in the examples to % are by weight (wt %).

Example 1

A reactor was charged with 0.231 kg of gypsum dihydrate and 0.149 kg of calcium hydroxide, brought to 10.16 kg with water, and sufficient stirring was carried out. Subsequently, 1.6 kg of JIS No. 3 sodium silicate, 0.143 kg of 48% sodium hydroxide and 0.0164 kg of sodium aluminate were added under atmospheric pressure at 15° C. and sufficient stirring was carried out, thereby preparing a reaction product-containing aqueous slurry. The compounding ratio (molar ratio) of gypsum and the second calcium compound at this time was 1:1.5 (reaction step). And then, the reaction product was filtered, following which the reaction product was rinsed with water (water rinsing step). Then, water was added to the resulting aqueous cake, thereby preparing an aqueous slurry having a solids content of 5 wt %. This slurry was placed in an autoclave and hydrothermal treatment was carried out in a hermetically sealed state at 200° C. for 3.5 hours (hydrothermal treatment step). Following the completion of hydrothermal treatment, spray drying was carried out with a spray dryer (model R-2, from Sakamoto Giken Co., Ltd.) at an inlet temperature of 200° C. and an outlet temperature of 50° C. and a disk rotational speed of 10,000 rpm (spray-drying step). This gave a sample for Example 1 (Si/Ca molar ratio, 1.6).

Example 2

Aside from using 0.288 kg of gypsum dihydrate and 0.124 kg of calcium hydroxide as the calcium feedstock (compounding ratio (molar ratio) of gypsum and second calcium compound, 1:1), the same steps were carried out as in Example 1, giving a sample for Example 2 (Si/Ca molar ratio, 1.8).

Example 3

Aside from using 0.385 kg of gypsum dihydrate and 0.083 kg of calcium hydroxide as the calcium feedstock (compounding ratio (molar ratio) of gypsum and second calcium compound, 1:0.5), the same steps were carried out as in Example 1, giving a sample for Example 3 (Si/Ca molar ratio, 1.9).

Example 4

Aside from using 0.433 kg of gypsum dihydrate and 0.062 kg of calcium hydroxide as the calcium feedstock (compounding ratio (molar ratio) of gypsum and second calcium compound, 1:0.3), the same steps were carried out as in Example 1, giving a sample for Example 4 (Si/Ca molar ratio, 1.9).

Example 5

Aside from using 0.481 kg of gypsum dihydrate and 0.041 kg of calcium hydroxide as the calcium feedstock (compounding ratio (molar ratio) of gypsum and second calcium compound, 1:0.2), the same steps were carried out as in Example 1, giving a sample for Example 5 (Si/Ca molar ratio, 2.3).

Example 6

Aside from using 0.385 kg of gypsum dihydrate and 0.164 kg of calcium chloride dihydrate as the calcium feedstock (compounding ratio (molar ratio) of gypsum and second calcium compound, 1:0.5), the same steps were carried out as in Example 1, giving a sample for Example 6 (Si/Ca molar ratio, 2.3).

Example 7

Aside from using 0.385 kg of gypsum dihydrate and 0.264 kg of calcium nitrate tetrahydrate as the calcium starting materials (compounding ratio (molar ratio) of gypsum and second calcium compound, 1:0.5), the same steps were carried out as in Example 1, giving an Example 7 sample (Si/Ca molar ratio, 2.3).

Example 8

Aside from using 0.553 kg of gypsum dihydrate and 0.079 kg of calcium hydroxide as the calcium feedstock (compounding ratio (molar ratio) of gypsum and second calcium compound, 1:0.3), the same steps were carried out as in Example 1, giving a sample for Example 8 (Si/Ca molar ratio, 1.8).

Example 9

Apart from carrying out spray drying using a different spray dryer (model OUDL-16, available from Ohkawara Kakohki Co., Ltd.) at an inlet temperature of 250° C., an outlet temperature of 125° C. and a disk rotational speed of 15,000 rpm, the same steps were carried out as in Example 3, giving a sample for Example 9.

Example 10

Aside from carrying out spray drying using a different spray dryer (model OUDL-16, available from Ohkawara Kakohki Co., Ltd.) at an inlet temperature of 250° C., an outlet temperature of 125° C. and a disk rotational speed of 20,000 rpm, the same steps were carried out as in Example 3, giving a sample for Example 10.

Example 11

A reactor was charged with 117 kg of gypsum dihydrate and 10 kg of calcium hydroxide, brought up to 2,464 kg with water, and sufficient stirring was carried out. And then, 370 kg of JIS No. 3 sodium silicate, 34 kg of 48% sodium hydroxide and 4 kg of sodium aluminate were added under atmospheric pressure at 15° C. and sufficient stirring was carried out, thereby preparing a reaction product-containing aqueous slurry. The compounding ratio (molar ratio) of gypsum and the second calcium compound at this time was 5:1 (reaction step). Subsequently, the reaction product was filtered using a filter press, following which the reaction product was rinsed with water (water rinsing step). Next, water was added to the resulting aqueous cake, thereby preparing an aqueous slurry having a solids content of 7 wt %. This slurry was placed in an autoclave and hydrothermal treatment was carried out in a hermetically sealed state at 200° C. for 3.5 hours (hydrothermal treatment step). Following the completion of hydrothermal treatment, spray drying was carried out by disk drying with a spray dryer (model ODT-62 Spray Dryer, from Ohkawara Kakohki Co., Ltd.) at an inlet temperature of 280° C. and an outlet temperature of 100° C. and a disk rotational speed of 7,000 rpm (spray-drying step). A sample for Example 11 (Si/Ca molar ratio, 2.2) was obtained from the chamber of the spray dryer.

Example 12

After the spray-drying step in Example 11, the dry material separated with a cyclone was collected, giving a sample for Example 12 (Si/Ca molar ratio, 2.1).

Example 13

The same steps as in Example 11 were carried out up to the hydrothermal treatment step. In the spray-drying step, aside from carrying out spray drying at an inlet temperature of 380° C. and an outlet temperature of 140° C. by nozzle drying with the spray dryer, the same steps were carried out as in Example 11, giving a sample for Example 13 (Si/Ca molar ratio, 2.2).

Comparative Example 1

FLORITE R (Lot No: S1001E, from Tomita Pharmaceutical Co., Ltd.) was used as the sample. This sample, which is the equivalent of FLORITE R from the former Tokuyama Corporation, is calcium silicate having a petaloid (corolloid) shape and composed of gyrolite-type calcium silicate and amorphous silicon dioxide (Si/Ca molar ratio, 2.3; average particle diameter, 33 μm).

Comparative Example 2

FLORITE R (Lot No: S1001E) of Comparative Example 1 was subjected to dry compression granulation (roll pressure, 15 MPa; roll speed, 5 rpm; screw speed, 20 rpm) using a roller compacter (TF-MINI Type II, from Freund Corporation), and the particle size was regulated by passing the granulated material through a 30 mesh screen on an oscillator. The material was then classified on a 80-mesh sieve and a 140-mesh sieve, and the portion of the dry granulated material remaining on the 140-mesh sieve was collected, thereby giving a sample for Comparative Example 2 (average particle diameter, 160 μm).

Comparative Example 3

Aside from using only 0.577 kg of gypsum dihydrate as the calcium raw material (compounding ratio (molar ratio) of gypsum and second calcium compound, 1:0), the same steps were carried out as in Example 1, giving a sample for Comparative Example 3 (Si/Ca molar ratio, 2.3).

Comparative Example 4

Aside from using only 0.248 kg of calcium hydroxide as the calcium raw material (compounding ratio (molar ratio) of gypsum and second calcium compound, 0:1), the same steps were carried out as in Example 1, giving a sample for Comparative Example 4 (Si/Ca molar ratio, 1.5).

Comparative Example 5

Aside from using 0.192 kg of gypsum dihydrate and 0.166 kg of calcium hydroxide as the calcium raw materials (compounding ratio (molar ratio) of gypsum and second calcium compound, 1:2), the same steps were carried out as in Example 1, giving a sample for Comparative Example 5 (Si/Ca molar ratio, 1.8).

Comparative Example 6

Aside from using 0.525 kg of gypsum dihydrate and 0.023 kg of calcium hydroxide as the calcium starting materials (compounding ratio (molar ratio) of gypsum and second calcium compound, 1:0.1), the same steps were carried out as in Example 1, giving a sample for Comparative Example 6 (Si/Ca molar ratio, 2.2).

Test Example 1

The Si/Ca molar ratio, average particle diameter, average particle diameter after treatment, percent change in average particle diameter, oil absorption, angle of repose, bulk specific volume and powder x-ray diffraction pattern were measured for each of the samples obtained in the examples and the comparative examples. The results are shown in Tables 1 and 2. In addition, as an illustration of the results of powder x-ray diffraction analysis, FIG. 1 shows the x-ray diffraction pattern obtained for the sample obtained in Example 3. FIGS. 2 to 6 show the results of scanning electron microscopy on the samples obtained in Examples 3 and 5 and Comparative Examples 1, 2 and 3. The methods used to carry out the respective measurements are described below.

(1) Si/Ca Molar Ratio (1-1) Quantitative Determination of Silicon Dioxide

The sample to be analyzed was dried and about 0.4 g was precisely weighed out and placed in a beaker, following which 20 mL of water and 10 mL of perchloric acid were added and the mixture was heated until white fumes arose. The beaker was then covered with a watch glass and heated further for 15 minutes. After the contents of the beaker had cooled, 30 mL of water was added and the mixture was filtered with quantitative filter paper (grade 5C), following which the residue was washed with 1 L of hot water. The filtrate and the washing liquid were combined, giving Liquid A. The residue on the filter paper was placed together with the filter paper in a platinum crucible and gradually dried under applied heat, ashed, and heated strongly at 900 to 1000° C. The residue was then allowed to cool in a desiccator and the weight W (g) was measured. Consequently, 5 drops of sulfuric acid and 15 mL of hydrofluoric acid were added to the residue, following which the residue was carefully heated to dryness, then heated at about 1000° C. to a constant weight and allowed to cool in a desiccator, whereupon the weight w (g) was measured. The silicon dioxide content was calculated from the following formula.

Silicon dioxide content (%)=[(W (g)−w (g))/weight of collected sample (g)]×100

(1-2) Quantitative Determination of Calcium Oxide

Liquid A obtained in the quantitative determination of silicon dioxide was neutralized with a 1 mol/L sodium hydroxide solution and, while stirring the neutralized solution, about 10 mL of a 0.05 mol/L EDTA solution was added using a 50 mL burette. And then, 15 mL of a 1 mol/L sodium hydroxide solution and 300 mg of hydroxynaphthol blue were added, and titration was carried out with a 0.05 mol/L EDTA solution. The time when the reddish-violet color of the solution completely disappeared and the solution turned blue was taken to be the endpoint. The titration volume V (mL) was read off at this time, and the content was determined from the formula shown below.

0.05 mol/L EDTA solution 1 mL=2.804 mg of CaO

Calcium oxide content (%)=[2.804 (mg/mL)×V (mL)×F/weight of collected sample (mg)]× 100(%)

where F: 0.05 mol/L EDTA solution factor (1-3) Si/Ca Molar Ratio

The Si/Ca molar ratio was calculated from the following formula using the value obtained by the above quantitative determination.

Si/Ca molar ratio=(silicon dioxide content (%)/molecular weight of silicon dioxide)/(calcium oxide content (%)/molecular weight of calcium oxide)

(2) Average Particle Diameter, Average Particle Diameter After Treatment, and Percent Change in Average Particle Diameter (2-1) Average Particle Diameter A sample was charged into a laser diffraction-type particle size analyzer (MT 3300 EXII, from Microtrac) so as to set a DV value within the range of 0.1-0.6 and circulated at a flow rate of 32.5 mL/s for 10 seconds, following which measurement was carried out twice in purified water over a measurement time in each instance of 20 seconds and the average of the two $D_{50}$ values was computed. This procedure was carried out three times, and the overall average of the results was treated as the average particle diameter. In addition, the standard deviation of the three measured values was calculated.

The DV (Diffraction Volume) value is a value that serves as an indicator of the measured density and relates to the Concentration Index, as captured by a detector positioned in front of the laser (see Nikkiso Co., Ltd. home page at http://www.nikkiso.co.jp). In this apparatus, by controlling the DV value within the range of 0.1 to 0.6 that is optimal for the sample being tested, the average particle diameter can be more accurately measured.

(2-2) Average Particle Diameter After Treatment

A sample was charged into a laser diffraction-type particle size analyzer so as to set a DV value within the range of from 0.1 to 0.6 and circulated for 5 minutes at a flow rate of 32.5 mL/s, following which measurement was carried out twice in purified water over a measurement time in each instance of 20 seconds and the average of the two $D_{50}$ values was computed. This procedure was carried out three times, and the overall average of the results was treated as the average particle diameter. In addition, the standard deviation of the three measured values was calculated. The meaning of the DV value is as indicated above in section (2-1).

(2-3) Percent Change in Average Particle Diameter

Using the average particle diameter and the average particle diameter after treatment values, the percent change in the average particle diameter after treatment was calculated from the following formula.

Percent change (%) in average particle diameter= [(average particle diameter (μm)−average particle diameter after treatment (μm))/average particle diameter (μm)]×100(%)

(3) Oil Absorption

This test was carried out as described below within a chamber controlled to 25° C., in accordance with the method of measuring oil absorption described in JIS K 5101-13-1. The sample was weighed out in an amount of 1.0 g and placed on a black plastic board. Next, boiled linseed oil that had been placed in a burette was added dropwise to the sample from above, 4 or 5 drops at a time, and was thoroughly kneaded with the powder each time using a spatula. When the entire amount had become a hard putty-like mass, the mass was kneaded each time a single drop was added, and addition was stopped just before the material suddenly softens with the last drop. The amount of boiled linseed oil that had been added was read off at this time, and the oil absorption was calculated from the following formula.

Oil absorption (mL/g)=volume of boiled linseed oil added (mL)/sample weight (g)

(4) Angle of Repose

The sample was dropped a little at a time onto a 50 mm diameter dish from a height of 100 mm. When the height of the pile of dropped sample stabilized, the pile height was measured and the angle of repose was calculated. The angle of repose was calculated from the formula shown below. The angle of repose is used as an indicator of flowability. According to Carr's index, at an angle of repose of 45° or less, the sample has a flowability suitable for manufacture.

Angle of repose (°)=$\tan^{-1}$ (pile height/dish radius (25 mm))

(5) Bulk Specific Volume

An amount of 2.0 g of sample was weighed out in and placed in a 50 mL measuring cylinder, after which tamping was carried out at a height of 4 cm and a speed of 100 times/250 seconds. The volume of the powder was then measured, and the bulk specific volume was calculated from the following formula.

Bulk specific volume (mL/g)=powder volume (mL)/ powder weight (g)

(6) Powder X-Ray Diffraction

Measurement was carried out with an x-ray diffractometer (SmartLab, from Rigaku Corporation) over the range of 2θ=5 to 90°. The measurement conditions were as follows: target, Cu; tube voltage, 40 kV; tube current, 30 mA; scan range, 5 to 90°; scan speed, 40.000°/min; scan steps, 0.02°; scan mode, continuous; kβ filter method; entrance slit, ⅔°; light-receiving slit, 10.0 mm.

(7) Scanning Electron Microscope

The sample was immobilized on carbon tape and gold metal evaporation was carried out thereon, giving a measurement specimen. Measurement was performed using a scanning electron microscope (JSM-5500LV, from JEOL, Ltd.), and secondary electron images (SEM images) were taken at an acceleration voltage of 15 kV.

As is apparent from the results in Table 1, the calcium silicates of Examples 1 to 10 had average particle diameters of from 40 to 190 μm, which are relatively large, and were able to exhibit excellent performances, including a percent change of 8% or less (in particular, 4% or less), an oil absorption of from 3.1 to 4.1 mL/g (in particular, from 3.4 to 4.1 mL/g), and an angle of repose of 45° or less (in particular, 40° or less). On the other hand, in a case where gypsum alone was used as the calcium starting material (that is, where a second calcium compound was not included) in the reaction step (Comparative Example 3), the average particle diameter was small, the percent change in the average particle diameter was large, and the particle strength was low. In a case where the second calcium compound alone was used as the calcium starting material (Comparative Example 4), although the average particle diameter was large and the particle strength was high, the oil absorption was low. Also, the granulated material obtained by dry compression granulating a conventional gyrolite-type calcium silicate (FLORITE R) (Comparative Example 2) had both a large average particle diameter and a high particle strength, yet a pronounced decrease in the oil absorption due to granulation was observed. As is apparent from the results in Table 2, similar outstanding advantages were obtained for

TABLE 1

| Test | Gypsum:Second calcium compound compounding ratio (molar ratio) | Si/Ca molar ratio | Average particle diameter (μm) | Average particle diameter after treatment (μm) | Percent change in average particle diameter (%) | Oil absorption (mL/g) | Angle of repose (°) | Bulk specific volume (mL/g) | Crystal form |
|---|---|---|---|---|---|---|---|---|---|
| Example 1 | 1:1.5 | 1.6 | 109 ± 2 | 108 ± 1 | 1 | 3.1 | 37 | 6.9 | GYR |
| Example 2 | 1:1 | 1.8 | 133 ± 2 | 128 ± 1 | 4 | 3.5 | 40 | 8.5 | GYR |
| Example 3 | 1:0.5 | 1.9 | 130 ± 3 | 125 ± 5 | 4 | 3.4 | 39 | 9.5 | GYR |
| Example 4 | 1:0.3 | 1.9 | 117 ± 6 | 118 ± 8 | −1 | 3.5 | 40 | 10.2 | GYR |
| Example 5 | 1:0.2 | 2.3 | 134 ± 5 | 133 ± 6 | 1 | 3.5 | 40 | 7.8 | GYR |
| Example 6 | 1:0.5 | 2.3 | 92 ± 2 | 87 ± 3 | 5 | 3.6 | 40 | 9.3 | GYR |
| Example 7 | 1:0.5 | 2.3 | 187 ± 14 | 178 ± 6 | 3 | 4.1 | 40 | 10.5 | GYR |
| Example 8 | 1:0.3 | 1.8 | 89 ± 2 | 82 ± 1 | 8 | 3.7 | 37 | 9.4 | GYR |
| Example 9 | 1:0.5 | 2.0 | 84 ± 2 | 81 ± 2 | 4 | 3.9 | 39 | 9.1 | GYR |
| Example 10 | 1:0.5 | 2.0 | 41 ± 0 | 41 ± 0 | 0 | 3.9 | 45 | 9.0 | GYR |
| Comp. Ex. 1 | — | 2.3 | 33 ± 1 | 33 ± 0 | 0 | 4.5 | 54 | 10.8 | GYR |
| Comp. Ex. 2 | — | 2.3 | 160 ± 2 | 157 ± 1 | 2 | 2.2 | 40 | 4.3 | GYR |
| Comp. Ex. 3 | 1:0 | 2.3 | 48 ± 1 | 38 ± 1 | 19 | 3.7 | 41 | 13.5 | GYR |
| Comp. Ex. 4 | 0:1 | 1.5 | 117 ± 1 | 116 ± 4 | 1 | 1.9 | 39 | 3.8 | GYR |
| Comp. Ex. 5 | 1:2 | 1.8 | 93 ± 1 | 92 ± 2 | 1 | 2.7 | 39 | 5.6 | GYR |
| Comp. Ex. 6 | 1:0.1 | 2.2 | 115 ± 18 | 62 ± 6 | 46 | 4.5 | 41 | 15.0 | GYR |

*In the table, "GYR" stands for gyrolite-type calcium silicate.

TABLE 2

| Test | Gypsum:Second calcium compound compounding ratio (molar ratio) | Si/Ca molar ratio | Average particle diameter (μm) | Average particle diameter after treatment (μm) | Percent change in average particle diameter (%) | Oil absorption (mL/g) | Angle of repose (°) | Bulk specific volume (mL/g) | Crystal form |
|---|---|---|---|---|---|---|---|---|---|
| Example 11 | 1:0.2 | 2.1 | 181 ± 7 | 163 ± 11 | 7 | 4.0 | 33 | 12.8 | GYR |
| Example 12 | 1:0.2 | 2.2 | 90 ± 1 | 87 ± 3 | 5 | 3.9 | 38 | 10.7 | GYR |
| Example 13 | 1:0.2 | 2.2 | 264 ± 3 | 241 ± 3 | 9 | 4.1 | 34 | 13.5 | GYR |

*In the table, "GYR" stands for gyrolite-type calcium silicate.

the calcium silicates of Examples 11 to 13 when manufacture was carried out with actual production equipment.

Furthermore, as is apparent by comparing FIG. 3 (Example 5) and FIG. 6 (Comparative Example 3), even though the Si/Ca molar ratio is the same at 2.3, when a second calcium compound was included together with gypsum (Example 5), large spherical particles were formed by spray drying and, because the particle strength was high, the shape of the particles was maintained. By contrast, when a second calcium compound was not included (Comparative Example 3), although large particles were formed by spray drying, the particle strength was low and so these large particles disintegrated into small particles.

Finally, as is clear also from FIG. 5 (Comparative Example 2), it was found that the granulated material obtained by dry compression granulating a conventional gyrolite-type calcium silicate (FLORITE R) become dense because the pore structure was collapsed by physical pressure during granulation. As a result, a marked decrease in oil absorption appears to have occurred.

What is claimed is:

1. Powdered gyrolite-type calcium silicate having:
   (1) an oil absorption of at least 2.8 mL/g;
   (2) an average particle diameter of at least 40 μm; and
   (3) a percent change in an average particle diameter of 15% or less after analysis with a laser diffraction particle size analyzer wherein the gyrolite-type calcium silicate is charged into the laser diffraction particle size analyzer so as to fall within a range of diffraction volume of from 0.1 to 0.6 and circulated at a flow rate of 32.5 mL/s for 5 minutes; and
   (4) an angle of repose of 45° or less.

2. The powdered gyrolite-type calcium silicate according to claim 1, comprising particles obtained by spray drying.

3. A method of manufacturing powdered gyrolite-type calcium silicate according to claim 1, comprising the steps of:
   (1) preparing a calcium-containing liquid feedstock by adding and mixing together gypsum and a calcium compound other than gypsum in an aqueous solvent;
   (2) mixing the calcium-containing liquid feedstock with a silicic acid-containing feedstock to obtain a reaction product;
   (3) subjecting an aqueous slurry containing the reaction product to a hydrothermal synthesis reaction to obtain gyrolite-type calcium silicate; and
   (4) spray-drying a dispersion liquid containing the gyrolite-type calcium silicate to obtain a gyrolite-type calcium silicate powder.

4. The manufacturing method according to claim 3, wherein the content of the calcium compound other than gypsum is from 0.11 to 1.99 moles per mole of gypsum.

5. The manufacturing method according to claim 3, wherein the calcium compound other than gypsum is at least one of:
   1) calcium hydroxide; and
   2) a calcium compound that reacts with an alkali ingredient to form calcium hydroxide.

6. The manufacturing method according to claim 5, wherein the calcium compound that reacts with an alkali ingredient to form calcium hydroxide is at least one of calcium chloride, calcium nitrate and calcium oxide.

7. The manufacturing method according to claim 3, comprising no granulation step other than spray drying.

8. The manufacturing method according to claim 3, wherein an aluminum compound has been added to the calcium-containing liquid feedstock and/or the silicic acid-containing feedstock.

9. The powdered gyrolite-type calcium silicate according to claim 1, wherein the average particle diameter of the powdered gyrolite-type calcium silicate is 109 μm to 300 μm.

10. The powdered gyrolite-type calcium silicate according to claim 1, wherein powdered gyrolite-type calcium silicate is produced by reacting silicate compound with calcium compounds consisting of gypsum and other calcium compounds, and wherein the content of the other calcium compounds is from 0.11 to 1.99 moles per mole of gypsum.

11. The powdered gyrolite-type calcium silicate according to claim 1, wherein powdered gyrolite-type calcium silicate contains a gyrolite-type crystal structure by X-ray diffraction analysis.

12. The powdered gyrolite-type calcium silicate according to claim 1, wherein the bulk specific volume is 8.5 mL/g or higher.

* * * * *